United States Patent
LaVon et al.

[11] Patent Number: 5,817,081
[45] Date of Patent: Oct. 6, 1998

[54] ABSORBENT ARTICLES FOR FLUID MANAGEMENT

[75] Inventors: Gary Dean LaVon, Middletown; Margaret Henderson Hasse; Gerald Alfred Young, both of Cincinnati; Bret Darren Seitz, West Chester, all of Ohio

[73] Assignee: The Procter & Gamble Company, Cincinnati, Ohio

[21] Appl. No.: 883,810

[22] Filed: Jun. 27, 1997

Related U.S. Application Data

[63] Continuation of Ser. No. 521,556, Aug. 30, 1995, abandoned, which is a continuation-in-part of Ser. No. 370,900, Jan. 10, 1995, abandoned.

[51] Int. Cl.[6] ............................................ A61F 13/15
[52] U.S. Cl. .......................... 604/378; 604/369; 604/358
[58] Field of Search ................................ 604/358, 378, 604/385.1, 369

[56] References Cited

U.S. PATENT DOCUMENTS

| | | |
|---|---|---|
| Re. 32,957 | 6/1989 | Elias . |
| 3,916,900 | 11/1975 | Breyer et al. . |
| 4,029,100 | 6/1977 | Karami . |
| 4,047,531 | 9/1977 | Karami . |
| 4,097,943 | 7/1978 | O'Connell . |
| 4,102,340 | 7/1978 | Mesek et al. . |
| 4,200,103 | 4/1980 | Black et al. . |
| 4,223,677 | 9/1980 | Anderson ................................ 604/378 |
| 4,269,188 | 5/1981 | Nishizawa et al. . |
| 4,282,874 | 8/1981 | Mesek . |
| 4,287,251 | 9/1981 | King et al. . |
| 4,333,464 | 6/1982 | Nakano . |
| 4,381,783 | 5/1983 | Elias . |
| 4,411,660 | 10/1983 | Dawn et al. . |
| 4,559,050 | 12/1985 | Iskra . |
| 4,560,379 | 12/1985 | Stemmler . |
| 4,657,538 | 4/1987 | Becker et al. . |
| 4,699,649 | 10/1987 | Bernardin . |
| 4,778,459 | 10/1988 | Fuisz . |
| 4,798,603 | 1/1989 | Meyer et al. . |
| 4,842,594 | 6/1989 | Ness . |
| 4,880,419 | 11/1989 | Ness . |
| 4,883,481 | 11/1989 | Blanchard . |
| 4,973,325 | 11/1990 | Sherrod et al. ................. 604/385.1 |
| 4,988,344 | 1/1991 | Reising et al. ................... 604/368 |
| 4,994,037 | 2/1991 | Bernardin . |
| 5,009,650 | 4/1991 | Bernardin . |
| 5,009,653 | 4/1991 | Osborn, III . |
| 5,037,409 | 8/1991 | Chen et al. ....................... 604/358 |
| 5,069,676 | 12/1991 | Ito et al. . |
| 5,139,841 | 8/1992 | Makoui et al. . |
| 5,141,794 | 8/1992 | Arroyo . |
| 5,147,345 | 9/1992 | Young et al. ..................... 604/378 |
| 5,149,720 | 9/1992 | DesMarais et al. . |
| 5,188,624 | 2/1993 | Young, Sr. et al. . |
| 5,198,472 | 3/1993 | DesMarais et al. . |
| 5,260,345 | 11/1993 | DesMarais et al. . |
| 5,294,478 | 3/1994 | Wanek et al. . |
| 5,300,054 | 4/1994 | Feist et al. ...................... 604/385.1 |
| 5,304,161 | 4/1994 | Noel et al. . |
| 5,360,420 | 11/1994 | Cook et al. ....................... 604/378 |
| 5,364,382 | 11/1994 | Latimer et al. ................... 604/378 |
| 5,387,208 | 2/1995 | Ashton et al. .................. 604/385.1 |
| 5,505,719 | 4/1996 | Cohen et al. ..................... 604/372 |

FOREIGN PATENT DOCUMENTS

| | | |
|---|---|---|
| 293208B1 | 5/1988 | European Pat. Off. . |
| 558889A1 | 5/1990 | European Pat. Off. . |

*Primary Examiner*—John G. Weiss
*Assistant Examiner*—Dennis Ruhl
*Attorney, Agent, or Firm*—Dinsmore & Shohl LLP

[57] ABSTRACT

An absorbent structure comprising a lower acquisition component having an original dimension and positioned to receive body exudates, and a storage component interposed between the wearer and the lower acquisition component which has a recovery from wet compression and an ability to recover from wet compression. The lower acquisition component can also vertically wick body exudates. The components work together to partition exudates from the lower acquisition component. Also, the lower acquisition component can have a resistance to compression deflection.

21 Claims, 4 Drawing Sheets

ABSORBENT ARTICLES FOR FLUID MANAGEMENT

This is a continuation of application Ser. No. 08/521,556, filed Aug. 30, 1995, now abandoned which is a continuation-in-part of application Ser. No. 08/370,900, filed Jan. 10, 1995, now abandoned.

TECHNICAL FIELD OF THE INVENTION

The present invention relates generally to absorbent articles which are to acquire and retain aqueous body exudates discharged by a wearer. More particularly, the absorbent articles of this invention can be utilized to provide improved absorbent structures having a multi-layered absorbent structure that can handle relatively large amounts of discharged body exudates.

BACKGROUND OF THE PRESENT INVENTION

Absorbent articles, such as non-cloth, disposable diapers, have traditionally utilized structures with various configurations and materials to provide the requisite absorbency performance. Over the years, one objective in developing improved absorbent products has been to increase both the total absorbent capacity of the product, as well as the tenacity and reliability with which such products absorb and hold fluid loads. Another common objective has been to provide articles with less bulk, a better and more comfortable fit, and better aesthetics and ergonomics.

One way for improving the absorbency characteristics has been to utilize entangled masses of fibers, e.g., non-woven fibrous webs, which can imbibe and retain liquids, such as discharged body fluids and other body exudates, both by absorption (e.g., fluid is taken up by the fiber material itself) and by wicking (e.g., fluid is distributed through and stored in the capillary interstices between fibers). Typically, however, fibers of this type have had a limited storage capacity for fluids, a reduced rate of distributing fluids, and a limited ability to partition fluids from other materials.

A way for improving the absorbency characteristics of fibrous web structures has been to incorporate so-called superabsorbent polymers in the fibrous web structures which imbibe absorbed fluid and generally form a swollen hydrogel material which, in turn, serves to retain the fluid within the structure. Another way for improving the absorbency characteristics of absorbent products has been to utilize of polymeric foam materials as the fluid-storage element in the absorbent cores of such products. Although these materials have enhanced storage capacity, they can lose their flexibility, become firm, and/or create an overall "heavy" or concentrated feeling when saturated with fluid. Furthermore, when adjacent to a polymeric film, such as used with a backsheet in a diaper, polymeric foams, such as those utilized as the storage component of the present invention, tend to cling to the film, which result in relatively poor aesthetics. Similarly, storage components with high concentrations of polymeric gelling material tend to have a wet, slimy texture when in contact with the polymeric film.

While fiber or fiber hydrogel absorbent structures can provide improved storage characteristics, they can have shortcomings in transporting or distributing absorbed body exudates from one region or zone to another for optimal performance and comfort. This can be troublesome in some products where body exudates are frequently discharged in discrete gushes over periods of time, and each gush of exudate discharged in this manner will generally encounter an absorbent structure with diminished capabilities to quickly and efficiently: (1) acquire subsequent gushes of fluid, (2) move fluid from the common discharge area to other unused, unsaturated, or relatively dry parts of the absorbent component, (3) remain resistant to compression deflection, (4) recover from wet compression, and (5) partition exudates.

Despite the continuing need for improved body exudates acquisition and reliable and practical storage of absorbed body exudate materials, and in spite of the many and varied attempts to address aspects of these needs, there remains the problem of providing an absorbent product that maintains desirable performance and aesthetics (e.g., flexible and soft) when saturated with fluids and after being subjected to deformation forces. There similarly remains a continuing need for absorbent products which permit more effective and efficient use of the absorbent materials.

It is an object of the present invention to provide an absorbent article that remains flexible and soft when saturated with body exudates, and effectively masks the appearance and minimizes negative tactile characteristics of a saturated article.

Furthermore, it is a object of the present invention to provide an absorbent article with relatively good fluid wicking, partitioning or distribution characteristics, as well as improved fluid storage.

It is yet another object of the present invention to have an absorbent article providing enhanced multidirectional fluid distribution of absorbed materials.

Additional objects, advantages, other features of the invention will be set forth and will become apparent through the description that follows, and, in part, will become apparent to those skilled in the art upon examination of the following, or may be learned with practicing the invention. The objects of the invention may be realized and obtained by means of the structures and combinations particularly pointed out in the appended claims.

SUMMARY OF THE INVENTION

The present invention relates to absorbent articles useful for absorbing and retaining body exudates of a user or wearer, and containing the exudates in an effective and efficient manner. An absorbent structure made in accordance with the present invention comprises a storage component interposed between a wearer and a lower acquisition component, wherein the lower acquisition component has a recovery from wet compression. In a preferred embodiment, the lower acquisition component has a resistance to compression deflection and can comprise a flexible hydrophilic structure of interconnected open spaces. In another preferred embodiment, the lower acquisition component is wider in the crotch portion than the crotch portion of other components of the absorbent structure. In a more preferred embodiment, the lower acquisition component is a hydrophilic flexible polymeric structure of interconnected open space.

In preferred embodiments, the storage component can comprise a flexible hydrophilic polymeric structure of interconnect open spaces, or in the alternative, a combination of a superabsorbent material incorporated into a fibrous web or tissue.

Absorbent articles made in accordance with the present invention can comprise an absorbent structure, a topsheet and a backsheet.

BRIEF DESCRIPTION OF THE DRAWINGS

The drawings, incorporated in and forming a part of the specification, illustrate several aspects of the present invention, and together with the description, serve to explain the principles of the invention. In the drawings.

Reference will now be made in detail to the presently preferred embodiments of the invention, an example which is illustrated by the attached drawings.

DETAILED DESCRIPTION OF THE PREFERRED EMBODIMENT

Referring now to the drawing figures, wherein like numerals indicate like element throughout the views, there is shown a preferred embodiment of the present invention as it would be used in a disposable absorbent article, and, in particular, in a disposable diaper, which is used in the management of body exudates and is capable of absorbing significant quantities of discharged aqueous body exudates (e.g., fluids and solid materials), such as urine and feces.

As used herein, the term "absorbent article" refers to articles which absorb and contain body fluids, and more specifically, the term refers to articles which are placed against or in close proximity to the body of the wearer to absorb and retain various fluids, including those discharged from the body. It should be understood, however, that the present invention is also applicable for use in other disposable "absorbent articles" such as pantiliners, sanitary napkins, diapers, incontinence pads, bandages, wound dressings, bed pads, tampons and the like. As used herein, the term "disposable absorbent article" refers to articles which are intended to absorb and contain fluids, such as those discharged from the body (e.g., blood, menses, urine, feces and the like), and further, which articles are intended to be discarded after a single use. (e.g., they are not intended to be laundered or otherwise restored and then reused).

Figure 1:
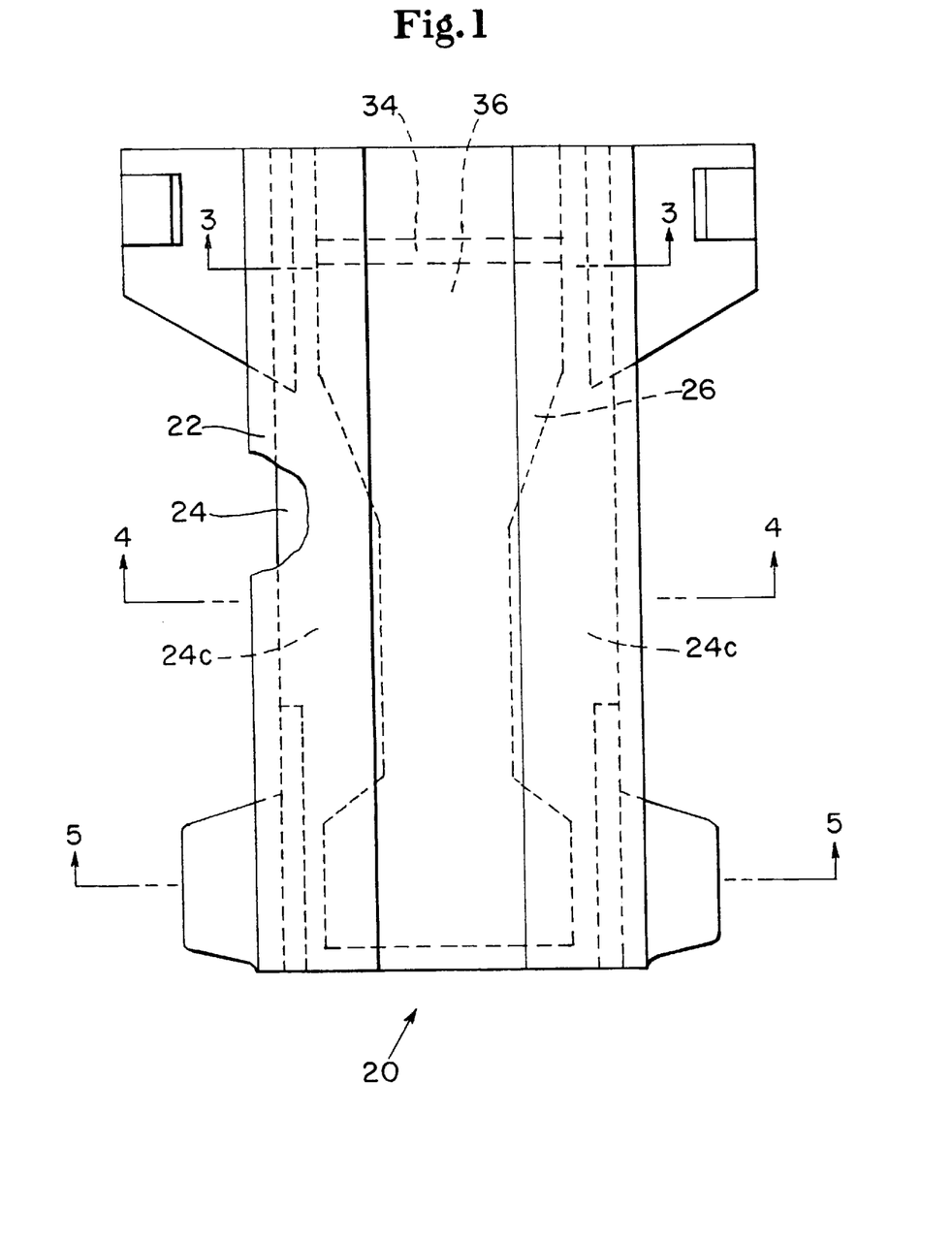
FIG. 1 is a top plan view of an exemplary absorbent article made in accordance with the present invention.
Figure 2:
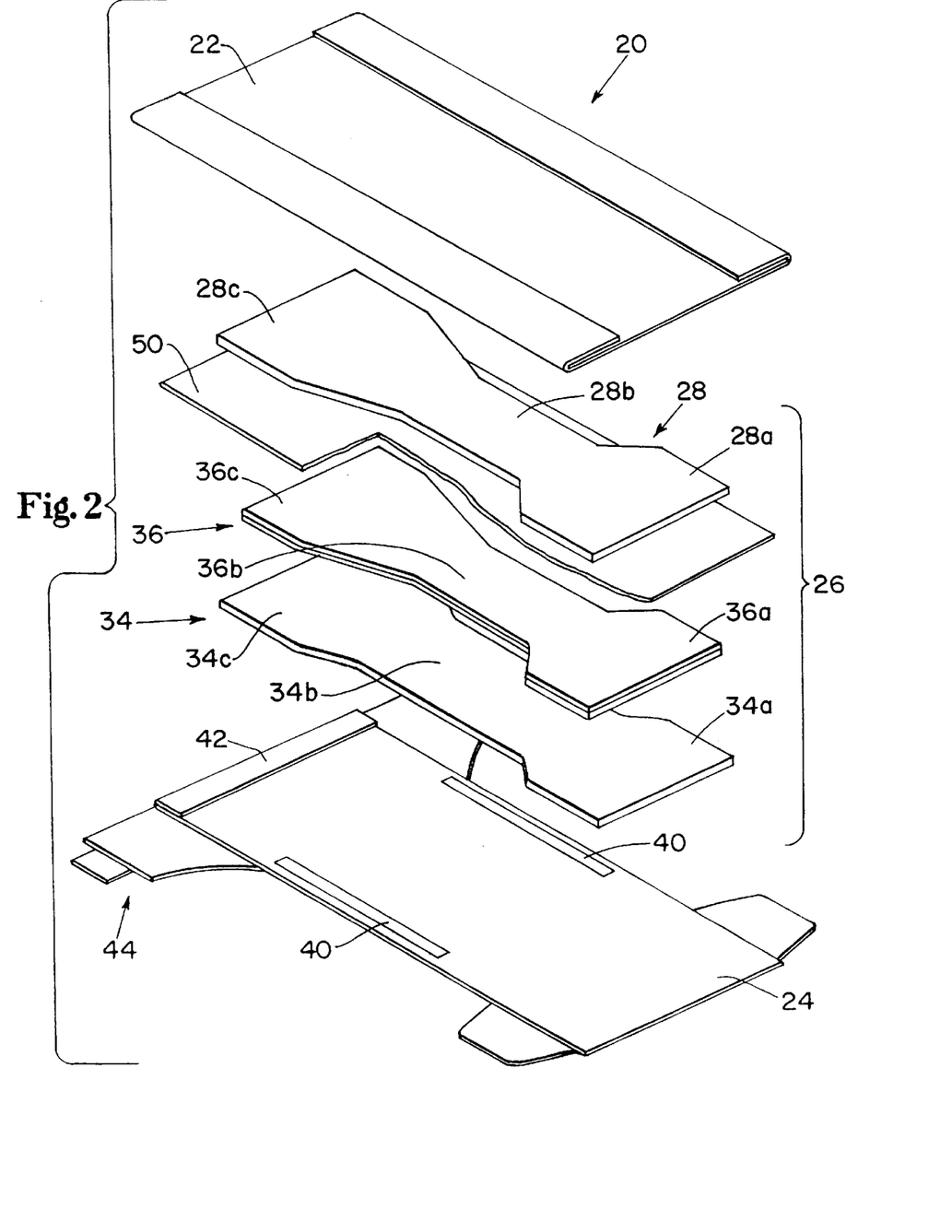
FIG. 2 is an exploded perspective view of the absorbent article of FIG. 1.

Regardless of the ultimate product configuration, absorbent articles generally comprise three basic structural elements; a backsheet, an absorbent structure which itself comprises one or more distinct components or layers, and a topsheet. A preferred absorbent article of the present invention is identified in FIGS. 1–7 as a disposable diaper (e.g., 20) comprising an absorbent structure 26, a topsheet 22, and a backsheet 24, each of which will be discussed in greater detail below. In addition to these elements, FIG. 2 illustrates a disposable diaper 20 having optional elements, such as leg elastic members 40, waist elastic member 42 and fastening element 44, which may be assembled in a variety of well-known diaper configurations.

It should be recognized, however, that in products other than disposable diapers, the present invention may be utilized with additional components, or without certain individual components, such as the topsheet, the backsheet, the elastic: members, or other optional elements known in the art. For example, an incontinence pad might preferably include no elastic portions. The desirability of including such particular elements in other absorbent products would depend upon their intended use.

A. Backsheet

Figure 3:
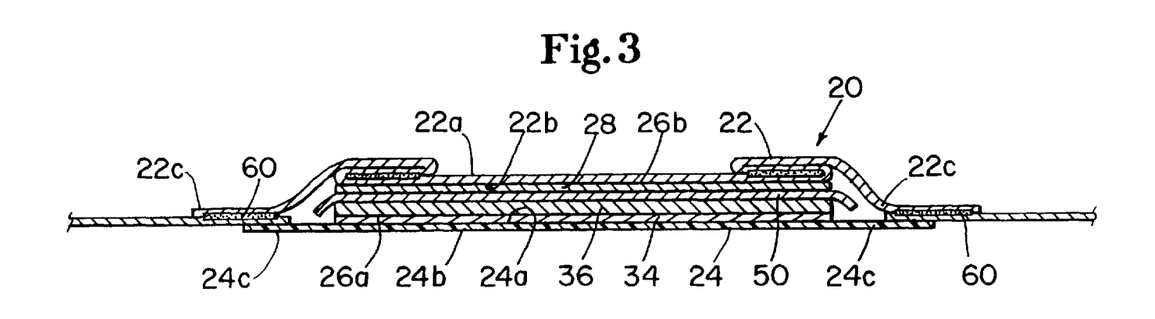
FIG. 3 is a cross-sectional view of the absorbent article of FIG. 1 taken along line 3—3 thereof.
Figure 4:
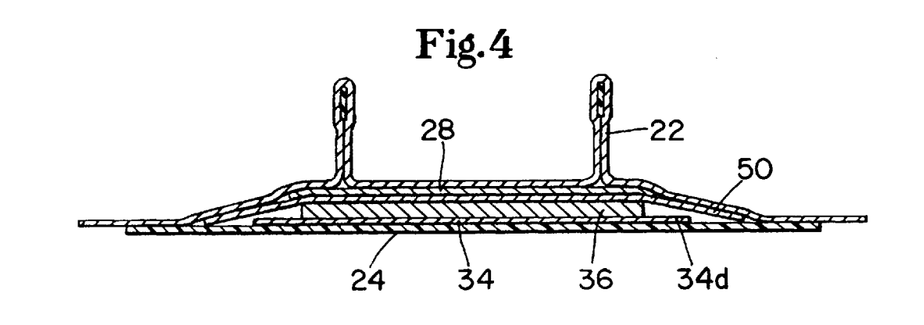
FIG. 4 is a cross-sectional view of the absorbent article of FIG. 1 taken along line 4—4 thereof.
Figure 5:
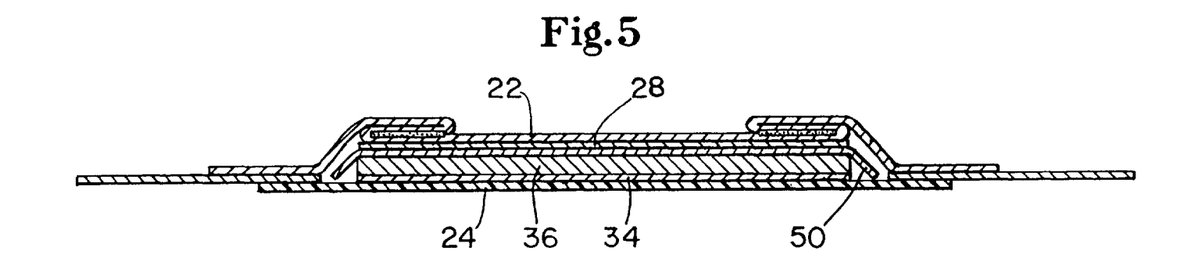
FIG. 5 is a cross-sectional view of the absorbent article of FIG. 1 taken along, line 5—5 thereof.

As stated previously, absorbent article 20 comprises a backsheet 24 which can be superimposed and co-extensive on its structure facing side 24a, as shown in FIGS. 3–5, with the backing face side 26a of the absorbent structure 26. The backsheet 24 is preferably constructed from a thin, plastic film of a flexible material which is substantially water impervious, and prevents collected discharged exudates from moving though and escaping from the absorbent article 20. Such a material may also be impervious to malodorous gases generated by body discharges which, in turns reduces the opportunity for discharged gases to directly escape and become noticeable to the wearer and others. Alternatively, the material may permit vapors to escape from the article 20 (e.g., breathable) while still preventing body exudates from passing therethrough. The backsheet 24 is preferably embossed and/or matted finished to provide a cloth-like appearance.

Illustrative examples of suitable materials which may be used as backsheet 24 include substantially hydrophobic non-woven materials, polymeric films, such as thermoplastic films of polyethylene, polypropylene or combinations thereof, which have a thickness of between about 0.0005" to about 0.003," (0.01 to 0.08 mm) and preferably a thickness of between about 0.001" to about 0.002" (0.03 to 0.05 mm). Other examples of suitable materials usable as backsheet 24 include a film-coated non-woven material, or a polyethylene having an embossed caliper of approximately 0.0015" (0.04 mm). Particularly preferred materials for the backsheet 24 include RR8220 blown film and RR5475 cast films as manufactured by Tredegar Industries, Inc. of Terre Haute, Ind.

The overall shape of the backsheet 24 should be elongated and could be configured in a number of ways, including a rectangular shape or a dog bone, an hourglass, or an elongated pear shape.

As illustrated in FIG. 1, and FIGS. 3 through 5, the backsheet 24 preferably has a width dimension which is greater than the width of the absorbent structure 26, thereby providing side marginal portions 24c of the backsheet 24 which extend beyond the longitudinal edges of the absorbent structure 26.

When the absorbent article 20 is worn by a wearer, the opposing ends of the backsheet 24 are fastened together using a fastening element 44, seen in FIG. 2, so that these ends join to form a circle around the wearer's waist.

B. Topsheet

Topsheet 22 can be superimposed and co-extensive on its structure facing side 22b, as seen best in FIGS. 3–5, with topsheet face side 26b of the structure 26, and has a body facing side 22a which should be positioned closest to or next to the skin of the wearer adjacent to the body orifice or wound to initially receive discharged body exudates. The topsheet 22 should be liquid pervious and comprise relatively hydrophobic materials (in comparison with the other materials of the absorbent structure 26) which, in turn, permit body exudates to rapidly penetrate and transfer through its thickness toward and into the absorbent structure 26. Topsheet 22 should also preferably comprise a material that has good strike through characteristics (e.g., little to no affinity for holding aqueous body exudates (e.g., fluids) in the area of contact between the topsheet 22 and the wearer's skin). The material should also reduce the tendency of the article 20 to rewet (e.g., allowing the fluids to flow back through the topsheet 22 to the wearer's skin), and should be a flexible material that is non-irritating to the wearer's skin.

A suitable topsheet 22 can be made of various materials, such as, synthetic fibers or films having a plurality of tapered capillaries of predetermined diameter and taper positioned in the topsheet 22 to permit flow of discharged exudates through the topsheet 22 into the underlying absorbent structure 26. Illustrative examples of suitable materials include polyester, polyolefin, rayon, or the like, or natural fibers such as cotton, foams, or combinations thereof In nonwoven topsheet materials, the fibers are typically bound together by a thermal binding procedure or by a polymeric binder, such as polyacrylate, and the structure which is substantially porous and permits fluids to readily pass therethrough into the underlying absorbent structure 26.

A preferred topsheet 22 is constructed from materials including polyester., rayon, rayon/polyester blends, polyethylene or polypropylene, and can be treated with a surfactant to make it more wettable and therefore relatively less hydrophobic, thereby facilitating fluid flow there through upon initial wetting.

The overall shape of the topsheet 22 can be configured in a number of ways, and will generally correspond with the shape of the backsheet 24. The topsheet 22 preferably has a width dimension greater than the width of structure 26, thereby, providing side marginal portions 22c which extends beyond the longitudinal edges of structure 26 so that the backsheet 24 and topsheet 22 can be joined together in the side marginal portions 22c and 24c in any suitable manner known in the art, (e.g., hot melt, as shown by numeral 60) either directly or joined intermediate members of the article 20 to form a seal for article 20.

C. Absorbent Structure

The absorbent structure 26 absorbs body exudates and preferably redistributes the body exudates for optimal storage while holding absorbed load of body exudates and maintaining comfort and nonirritation for the wearer's skin. To function as an effective disposable diaper, the size and configuration of structure 26 can be altered to meet absorbent capacity requirements depending on the intended use of article 20.

The absorbent structure 26, having a backing face side 26a and a topsheet face side 26b, can comprise one or more distinct elements interposed between the backsheet 24 and the topsheet 22 to ensure proper absorption and containment of fluids. FIGS. 3–5 illustrate a preferred embodiment of the absorbent structure 26 essentially comprising two acquisition components, denoted as 28 and 34, and a storage component 36, wherein the upper and lower acquisition components 28 and 34, respectively, are positioned to receive body exudates and other fluids which have been discharged into the absorbent article 20 by the wearer, with or without the aid of gravity. The storage component 36, in turn, is interposed within the article 20 to be in fluid communication with and between the upper and lower acquisition components 28 and 34 so it can acquire body exudates from the acquisition components 28 and 34, and can redistribute, store, and hold the acquired body exudates. So long as the upper and lower acquisition components 28 and 34 and storage component 36 are in fluid communication with each other, they may be interposed relative to one another in a wide variety of configurations, and it is not necessary that both upper and lower acquisition components 28 and 34 be in direct contact with fluid storage component 36.

Additional intervening components can be positioned between the acquisition and storage components 28, 34, and 36 respectively. One example of an additional component is a fluid pervious sheet 50 (e.g., a tissue sheet or other scrim) that is positioned between the upper acquisition component 28 and the storage component 36 to increase the integrity of the upper acquisition component 28 during processing or use.

Figure 7:
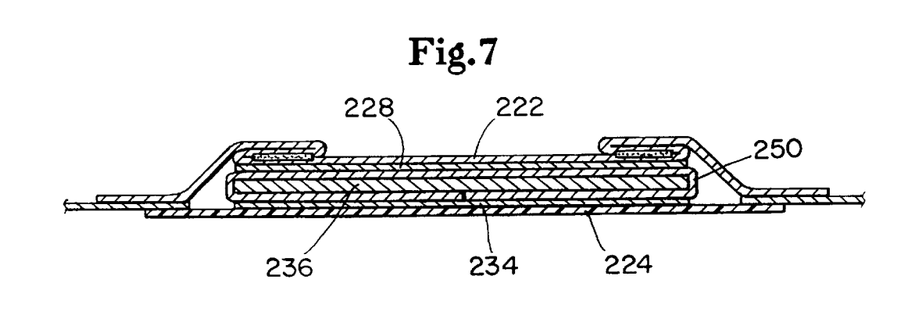
FIG. 7 is a transverse cross sectional view of another alternative embodiment of the present invention formed with tissue encasing the absorbent structure.

In another embodiment shown in FIG. 7, a fluid pervious sheet 250, (e.g., a tissue sheet or other scrim) can envelop all or part of the upper acquisition component 228 and/or the storage component 236, and can be interposed between the lower acquisition component 234 and the storage component 236 to further increase the integrity of the upper and lower acquisition components 228 and 234, or storage component 236, during processing and/or in use. Alternatively, fluid pervious sheets 250 simply can be interposed between the components 228 and 236, and/or components 234 and 236, as individual components. Nonetheless, body exudates must be able to move from the upper and lower acquisition components 29 or 228 and 34 or 234 through or around additional intervening components (e.g., 50 or 250) and into the storage component 36 or 236.

A preferred relationship between the acquisition components 28 and 34 and the storage component 36 is illustrated in FIGS. 3–5, and it should be understood that for purposes of this invention, these types of components refer merely to the zones of the absorbent structure 26 and are not necessarily limited to single, or even physically separate, layers or sheets of materials. Both the acquisition components 28 and 34 and the storage component 36 can comprise regions of different characteristics within a single structure, or may comprise laminates or combinations of several sheets or webs. In any structure, it is desirable to employ minimal amounts of the absorbent (e.g., acquisition or storage) materials in each of the respective components 28, 34 and 36 consistent with the need to provide adequate absorption, distribution and storage of body exudates with minimal leakage of such exudates from the absorbent article 20. The interaction of the particular configuration of acquisition and storage components 28, 34 and 36 utilized in the absorbent article 20 results in especially efficient handling of body exudates and, in turn, permits utilization of minimal amounts of absorbent or storage materials in each of the respective components 28, 34 and 36, while providing enhanced aesthetics.

1. Fluid Acquisition Components

As stated previously, absorbent structure 26 comprises an upper acquisition component 28 and a lower acquisition component 34. The upper acquisition component 28 is preferably positioned in close proximity to topsheet 22 and is interposed between the topsheet 22 and the fluid storage component 36. Since discharge of body exudates generally occurs in identifiable, discrete areas, the upper acquisition component 28 should preferably be aligned in overlying proximity with these areas so as to be effectively located to acquire and transport discharged body exudates to other regions of the structure 26. In disposable diapers, these discrete areas would correspond to the crotch area 28b and the front area 28a (e.g., the portion of the absorbent article 20 which is intended to be placed on the front of the wearer) of the acquisition component 28. For male wearers, it may be desirable for the upper acquisition component 28 to extend to near the front area 28a to effectively acquire the relatively high fluid load that occurs in the front area of an absorbent article 20, such as a diaper, and to compensate for directional variations of the discharges. In other corresponding absorbent articles (e.g. 20), the area encompassing upper acquisition component 28 will vary depending upon the design and fit of the absorbent article 20.

Figure 6:
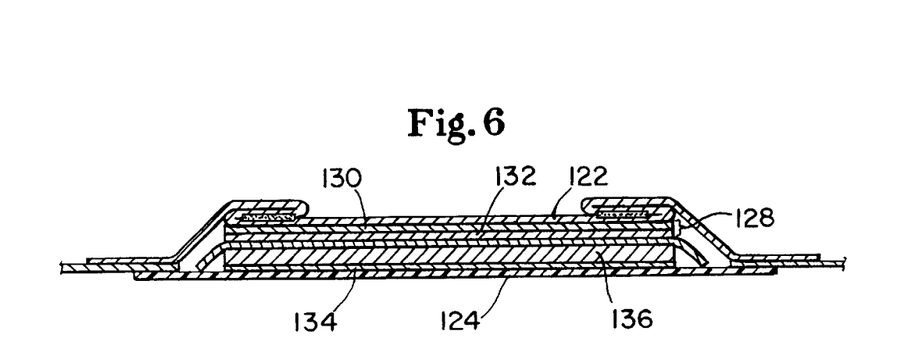
FIG. 6 is a transverse cross-sectional view of an alternative embodiment of a absorbent article of the present invention formed with a plurality of upper absorbent components.

An upper acquisition component may comprise more than one type of material having varying capillary or fluid distribution properties, and FIG. 6 illustrates an alternative upper acquisition component 128 having a first upper acquisition component 130 and a second upper acquisition component 132. For optimal efficiency of absorption, first upper acquisition component 130 is preferably interposed between the topsheet 122 and second upper acquisition component 132. In such a configuration, the first upper acquisition component 130 preferably comprises a material having larger relative cell sizes and a lower capillary suction specific surface area per volume, as discussed later herein, when compared with the material of the second upper acquisition component 132. The resulting relative differences between the materials provides a capillary suction gradient between the upper and lower components 130 and 132, respectively, and allows for absorbed exudates to be more quickly and efficiently absorbed from topsheet 122 and transported (e.g., wicked and partitioned) into the fluid storage component 136.

Although the relative size of the upper acquisition component 28 can vary, it should have a width sufficient to acquire periodic gushes of body fluids and to prevent direct discharge of exudates onto the fluid storage component 36. The upper acquisition component 28 is preferably positioned relative to the topsheet 22 and the storage component 36 such that the upper acquisition component 28 is of sufficient length and width to extend to areas corresponding at least to about 25%, preferably at least about 50%, of the surface area of the topsheet 22. Frequently, the surface area of the storage component 36 will range between about 25% to about 200%, preferably between about 50% to about 150%, more preferably between about 60% to about 125%, of the surface area of the upper acquisition component 28.

In a preferred embodiment for disposable diapers, the width at the front and back portions 28a and 28c of the upper acquisition component 28 is substantially the same as the width of the front and back portions 36a and 36c, respectively, of the storage component 36 and the front and back portions 34a and 34c, respectively, of the lower acquisition component 34. In one embodiment, the front and back portions 28a and 28c of the upper acquisition component 28 each have a width about 5.0" (12.7 cm), and the width distance narrows, for comfort, to about 2.5" (6.35 cm) in the crotch portion 28b.

The upper acquisition component 28 can be configured in any desired shape consistent with comfortable fit and the several sizing limitations discussed herein. Illustrative examples of suitable shapes for the acquisition component 28 include, circular, rectangular, trapezoidal or oblong, (e.g., hourglass-shaped, dog-bone-shaped, half-dog-bone-shaped, oval or irregularly shaped).

The lower acquisition component 34 is preferably positioned in close proximity to the storage component 36 and is interposed between storage component 36 and backsheet 24. When absorbent article 20 is provided without lower acquisition component 34, exudates not absorbed by the upper component 28 or the storage component 36 might collect in a pool on the core facing side 26a of structure 26 where exudates would be slowly absorbed by storage component 36, as compared to the rate of acquisition materials, as discussed in greater detail later, resulting in potentially leakage out of absorbent article 20.

In order to absorb exudates that have run off the upper acquisition component 28, or have escaped from the storage component 36, and to mask the storage component 36, the lower acquisition component 34 is preferably sized and configured to have a larger surface area than both the upper acquisition component 28 and storage component 36. The surface area of the upper acquisition component 28 can range from between about 15% to about 100% of the surface area of the lower acquisition component 34. Although the lower acquisition component 34 can have a length which corresponds to the length of the upper acquisition component 28, it will preferably be somewhat longer than the length of the storage component 36.

In contrast to the similar width dimensions of the components at the front and back portions of the absorbent article 26, as illustrated in FIGS. 3–5, FIG. 4 illustrates a preferred embodiment where the width dimension of the lower acquisition component 34 at the crotch portion 34b is greater than the width dimension of the upper acquisition component 28 and/or the storage component 36 at their respective crotch portions 28b and 36b. Preferably, the width dimension of the crotch portion 34b is at least about 5% greater than the width dimension of the crotch portions 28b and 36b, and provides an extended portion 34d which extends laterally beyond lateral edges of the upper acquisition component 28 and storage component 36.

The acquisition components 28 and 34 can also be of any desired shape consistent with comfortable fit and the sizing limitations, as discussed above. The acquisition components 28 and 34 can be configured in a similar shape to one another, but such is not required. They can also be a similar or different shapes than the shape of storage component 36.

The upper and lower acquisition components 28 and 34 each preferably comprise a material having a porous hydrophilic absorbent structure which has certain fluid handling characteristics with respect to exudates so that urine passes onto and into and so that the material serves to quickly collect and temporarily hold such exudates. Since such exudates are frequently discharged in gushes, the material must be able to quickly collect the exudates, with or without the aid of gravity, and must also preferably transport exudates (e.g., by wicking or other mechanisms) from the point of initial contact to other parts of the acquisition components 28 and 34 for eventual absorption into the storage component 36. Acquisition components 28 and 34, and preferably the lower acquisition component 34, will typically recover substantially to their original size, caliper, and shape after compression, and will be flexible, and will not lose their flexibility, or otherwise become stiff or hard, when saturated with fluid.

A particularly important attribute of the lower acquisition component 34 is thereby that it does not collapse when desorbed by the storage component 36 due to capillary or osmotic pressures. These capillary pressures should be insufficient to hold the acquisition component 34 in a collapsed state when mechanically compressed in a wet state. When dewatered, either by desorption or compression, air will fill the voids of the lower acquisition component 34 which restores the capacity of the lower acquisition component 34 allowing it to quickly acquire additional body exudates, as well as providing a drier feel to the lower acquisition component 34.

An important property of useful absorbent structures according to the present invention is their capillary absorption pressure. Capillary absorption pressure refers to the ability of the structure to wick fluid vertically. [See P. K. Chatterjee and H. V. Nguyen in "Absorbency," Textile Science and Technology, Vol. 7; P. K. Chatterjee, Ed.; Elsevier: Amsterdam, 1985; Chapter 2.] For the purposes of the present invention, the capillary absorption pressure of interest is the hydrostatic head at which the vertically wicked fluid loading is 50% of the free absorbent capacity under equilibrium conditions at 31° C.

Of particular importance to the ability of the absorbent structures of the present invention to function as useful fluid acquisition and distribution components is their capillary desorption pressure. Capillary desorption pressure refers to the structure's ability to hold onto fluid at various hydrostatic heads at equilibrium conditions at 22° C. For the purposes of the present invention, the capillary desorption pressure of interest is the hydrostatic head (i.e., height) at which the fluid loading is 50% of the free absorbent capacity under equilibrium conditions at 22° C.

The capillary desorption pressure is important relative to the absorption pressure of other elements of the absorbent article 20, especially those intended for fluid storage, such as storage component 36. If the acquisition components 28 and 34 hold the acquired exudates too tenaciously, this will inhibit the ability of the other components, such as storage component 36, to partition fluid away, thereby the acquisition components 28 and 34 remain loaded with exudates, and thus, the absorbent article 20 is more susceptible to leaks. This can cause the acquisition component to remain so heavily loaded with fluid that the absorbent article is more susceptible to leaking. The lower acquisition component 34 of the present invention needs to have desorption pressures low enough so that storage component 36 can effectively dry out (i.e. desorb) this lower acquisition component 34, which restores the capacity of the acquisition component 34 and allows it to accept further "gushes" (either from the wearer or from squeezed out exudates from the storage component 36). Additionally, it is important that the lower acquisition component 34 be substantially dry and non-collapsed in order to provide the aesthetics required from such a structure. Upper acquisition component 28 must efficiently desorb in order to keep the element (e.g., topsheet) next to the skin of the wearer comparatively dry. The acquisition components 28 and 34 of the present invention are readily desorbed by the storage component 36 having higher absorption pressures that store such exudates, as discussed later.

Vertical wicking (i.e., wicking in a direction opposite from gravitational forces) of fluid is an especially important performance attribute for the acquisition components 28 and 34. In the present invention, body exudates that are absorbed must be moved within the absorbent structure 26 from a relatively lower to a relatively higher position within the absorbent structure 26. It is presently preferred of the material of the lower acquisition component 34 vertically wick synthetic fluid (65±5 dynes/cm) about 5 cm in no more than about 90 seconds.

An important mechanical feature of the acquisition component 34 used in this invention is the strength of the material as determined by its resistance to compression deflection (RTCD). The lower acquisition component 34 must be suitably resistant to deformation or compression by forces encountered in use, or when engaged in the absorption and retention of fluids or other exudates. This is particularly important as fluids are partitioned, either due to a desorption pressure gradient or compression from the lower absorbent component 34 and into storage component 36. If the capillary desorption pressure of the lower acquisition component 34 is greater than its RTCD and/or its re-expansion strength (i.e., expansion pressure at a particular compression), it will tend to collapse upon desorption, and thus, leave the foam in a saturated, densified state, which can feel wet to the touch, and lead to wetter skin for the wearer. It would also impede the rate of acquiring additional fluid gushes. In a presently preferred embodiment, structures useful as lower acquisition component 34 exhibit a resistance to compression deflection such that a confining pressure of about 0.74 psi (5.1 kPa) produces a strain of from about 5% to about 85% compression, and preferably from about 5% to about 50% compression, of the lower acquisition component 34.

If the lower acquisition component 34 is too strong, it will look and feel stiff, leading to poor aesthetics. Also, a mechanism is used in the present invention which can distribute and partition fluids can involve mechanical pumping. Thus, it can be advantageous for the lower acquisition component 34 to be squeezed by normal pressures experienced by the wearer during use to promote additional partitioning into the storage component 36. The lower acquisition component 34 of the present invention should balance capillary desorption pressure and strength to avoid such undesirable collapse during partitioning.

Also, the lower acquisition component 34 should be able to recover from wet compression (RFWC), which relates to the tendency or propensity of a piece of wet material to quickly return to its original dimensions after being deformed or compressed under forces encountered in manufacture, transportation, or use, without having a reservoir of free fluid to draw from during re-expansion. It is presently preferred that the lower acquisition component 34 exhibit a recovery of at least about 60%, more preferably at least about 75%, and most preferably at least about 90%, of the original dimensions within two (2) minutes of being released from compression.

Another important property of lower acquisition component 34 of the present invention is its free absorbent capacity, which is the total amount of test fluid (synthetic urine) which it will absorb into its structure per unit mass of solid material. In absorbent articles 20, such as diapers, the lower acquisition component 34 of the present invention will at least meet a minimum free absorbent capacity, and to be especially useful in present invention, it should have a free capacity of from about 12 to about 125 g/g, preferably from about 20 to about 90 g/g, and most preferably from about 25 to about 75 g/g, of synthetic urine per gram of dry material. Jayco synthetic urine used is prepared by dissolving a mixture of 2.0 g KCl, 2.0 g $Na_2SO_4$, 0.85 g $NH_4H_2PO_4$, 0.15 g $(NH_4)_2HPO_4$, 0.19 g $CaCl_2$, and 0.23 g $MgCl_2$ to 1.0 liters with distilled water. The salt mixture can be purchased from Endovations, Reading, Pa. (cat No. JA-00131-000-01).

It should be noted that the absorbent article 20 can be assembled with the same material for the upper and lower absorption components 28 and 34, or these components can comprise different materials so long as the specific combinations serve the purposes described above. Particular examples of various combinations are discussed later.

i. Polymeric Foam

One type of material suitable as absorbent components 28 and 34, as well as 128, 130, 132, 228, and 234, is a polymeric foam material capable of acquiring and distributing body exudates, such as fluids, which comprises a hydrophilic, flexible, nonionic polymeric foam structure of interconnected opened spaces, as disclosed in commonly assigned, U.S. patent application, Ser. No. 08/370,695, filed Jan. 10, 1995 in the names of Keith J. Stone, et al., which has been allowed by the U.S. Patent Office, the disclosure of which is hereby incorporated herein by reference. Another such suitable polymeric foam material is disclosed in commonly-assigned, U.S. patent application, Ser. No. 08/521,566, Case 5807, filed Aug. 30, 1995 in the name of Thomas A. DesMarais, the disclosure of which is hereby incorporated herein by reference. Polymeric foams useful in absorbent articles of the present invention are those which are relatively open-celled, which means the individual cells of the foam are for the most part not completely isolated from each other by the polymeric material of the cell walls. The cells in such substantially open-celled foam structures have intercellular openings or "windows" that are large enough to permit ready fluid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." For purposes of the present invention, a foam material is "open-celled" if at least about 80% of the cells in the foam structure that are at least 1 micron in size are in fluid communication with at least one adjacent cell.

In addition to being open-celled, these polymeric foams are sufficiently hydrophilic to permit the foam to absorb aqueous fluids or other exudates. The internal surfaces of the foam structures are rendered hydrophilic by residual hydrophilizing surfactants left in the foam structure after polymerization, or by selected post-polymerization foam treatment procedures, both described in previously mentioned commonly assigned, copending U.S. patent applications Ser. No. 08/370,695, filed Jan. 10, 1995 in the names of Keith J. Stone, et al., and Ser. No. 08/521,566, Case 5807, filed Aug. 30, 1995 in the name of Thomas A. DesMarais.

The RTCD exhibited by the foams of the present invention is a function of the polymer modulus, as well as the density and structure of the foam network. The polymer modulus is, in turn, determined by: a) the polymer composition; b) the conditions under which the foam was polymerized (e.g., the completeness of polymerization obtained, specifically with respect to crosslinking); and c) the extent to which the polymer is plasticized by residual material, e.g., emulsifiers, left in the foam structure after processing. The RTCD can be quantified by determining the amount of strain produced in a sample of saturated foam held under a certain confining pressure for a specified period of time. Foams useful as absorbents for acquiring and distributing fluids are those which exhibit a resistance to compression deflection, such that a confining pressure of 0.74 psi (5.1 kPa) produces a strain of typically from about 5% to about 85% compression of the foam structure. Preferably the strain produced under such conditions will be in the range from about 5% to about 65%, and most preferably, from about 5% to about 50%.

Cell Size

A feature that can be useful in defining preferred polymeric foams is the cell structure. Foam cells, and especially cells that are formed by polymerizing a monomer-containing oil phase that surrounds relatively monomer-free water-phase droplets, will frequently be substantially spherical in shape, and are connected to each other by openings, which are referred to as holes between the cells. Both the size or "diameter" of such spherical cells and the diameter of the passages (hole) between the cells are commonly used for characterizing foams in general. Since the cells, and holes between the cells, in a given sample of polymeric foam will not necessarily be of approximately the same size; average cell and hole sizes, i.e., average cell and hole diameters, will often be specified.

Cell and hole sizes are foam parameters that can impact a number of important mechanical and performance features of the absorbent foams used with the present invention. Since the cell structure contributes to capillary suction specific surface area that, together with foam hydrophilicity, determines the capillarity of the foam, cell and hole sizes are foam structure parameters that can directly affect the fluid wicking properties of absorbent foams, as well as the capillary pressure that is developed within the foam structure.

The foams useful in the absorbent components 28 and 34 of the present invention will preferably have a number average cell size of from about 20 to about 200 $\mu$m, and typically from about 30 to about 130 $\mu$m, and a number average pore size of from about 5 to about 30 $\mu$m, and typically from about 8 to about 25 $\mu$m.

Capillary Suction Specific Area

"Capillary suction specific surface area" is a measure of the test-liquid-accessible surface area of the polymeric network accessible to the test fluid, and is determined both by the dimensions of the cellular units in the foam and by the density of the polymer, and is thus, a way of quantifying the total amount of solid surface provided by the foam network to the extent that such a surface participates in absorbency. The polymeric foams useful as the absorbent components 28 and 34 are those that have a capillary suction specific surface area of at least about 0.2 $m^2/g$. Typically, the capillary suction specific surface area is in the range from about 0.3 to about 4 $m^2/g$, preferably from about 0.3 to about 2.5 $m^2/g$, most preferably from about 0.3 to about 1.5 $m^2/g$.

Surface Area Per Foam Volume

Specific surface area per foam volume can be useful for empirically defining foam structures that will not collapse, or remain in a collapsed state, when desorbed, (e.g., dried or compressed) while in a wet state. See U.S. Pat. No. 5,387,207, issued Feb. 7, 1995 to Dyer, et al., the disclosure of which is hereby incorporated herein by reference, where specific area per foam volume is discussed in detail with regard to collapsed foams. As used herein, "specific surface area per foam volume" refers to the capillary suction specific surface area of the foam structure times its foam density in the expanded state. It has been found that certain maximum specific surface area per foam volume values correlate with the ability of the foam structure to remain in an expanded state when desorbed, or to quickly return to all expanded state after being compressed while in a wet state. Polymeric foams having specific surface area per foam volume values of about or less 0.06 $m^2/cc$, preferably from about 0.01 to about 0.04 $m^2/cc$, most preferably from about 0.01 to about 0.0:3 $m^2/cc$ are useful in the absorbent components 28 and 34 in the present invention.

Foam Density

"Foam density" (i.e., in grams of foam per cubic centimeter of foam volume in air) is specified herein on a dry basis and the amount of absorbed aqueous fluid left in the foam, (e.g., after HIPE polymerization, washing and/or hydrophilization), is disregarded in calculating and expressing foam density. Foam density does include, however, in fact other residual materials such as emulsifiers present in the polymerized foam and, such residual materials can contribute significant mass to the foam material.

The density of the foam, like capillary suction specific surface area, can influence a number of performance and mechanical characteristics of absorbent foams which includes the absorbent capacity for aqueous fluids and the compression deflection characteristics.

Polymeric foams for use in the present invention as fluid acquisition components 28 and 34 have dry basis density values in the range of from about 0.0079 to about 0.077 g/cc, preferably from about 0.011 to about 0.048 g/cc, and most preferably from about 0.013 to about 0.0322 g/cc The individual layer or layers of the polymeric foam material can also be provided having a slitted region, one or more slits extending at least partially through the thickness of the materials to form components 28 and 34 between the crotch portions 28b and 34b and the front portions 28a and 34a, as disclosed in U.S. Pat. No. 5,397,316, issued Mar. 14, 1995 to LaVon et al., the disclosure of which is hereby incorporated herein by reference. Slitting of the polymeric foam material is preferred for several reasons. Since a polymeric foam material expands as it absorbs fluids, the slitting of the material causes it to buckle open and form a well-like shape as it expands. This physical alteration also increases the rate of absorption from the topsheet 22 due to the increased surface area of the material, and even more desirable, the expanded material is more flexible and pliable, even when saturated with fluids.

ii. Airfelt

Besides a polymeric foam, another preferred type of material for use in or as the upper acquisition component 28 is an absorbent non-woven fibrous structure which provide the required fluid handling characteristics. In particular, non-woven structures fashioned from hydrophilic or hydrophilized fibers such as fibrous webs formed from cellulosic (e.g., wood pulp) fibers can be usefully employed as or in the upper acquisition component 28. Such webs for example are typically airlaid structures having a dry density of from about 0.04 to about 0.3 g/cm$^3$ and a basis weight of from about 0.015 to about 0.35 g/cm$^2$.

Other types of non-woven structures suitable for use as the upper acquisition component 28 comprise structures such as surfactant-treated bonded carded webs, webs of melt blown synthetic macrofibers or microfibers, pulp webs, staple fiber conformed webs and the like.

iii. Chemically Stiffened Cellulose Fiber

Another type of preferred material for use in or as the upper acquisition component 28 is one which is formed from treated cellulose fibers that impart certain dry density characteristics to the structures, and that is employed in appropriate basis weight. Non-woven fibrous absorbent structures which provide upper acquisition component 28 with the foregoing density and basis weight characteristics are preferably constructed essentially from hydrophilic chemically stiffened cellulosic fibers, that are typically wood pulp fibers which have been stiffened with an intrafiber chemical stiffening agent and otherwise processed so they are formed into a twisted, curled configuration, as discussed more fully in U.S. Pat. No. 5,217,445, to Young et al., the disclosure of which is hereby incorporated herein by reference. For purposes of this invention, the term "chemically stiffened fibers" means any fibers which have been treated by chemicals to increase stiffness of such fibers under both dry and aqueous conditions. Thus, materials preferred as the upper acquisition component 28 can comprise a non-woven fibrous web formed from about 50% to about 100%, or more preferably from about 75% to about 100%, by weight of the web of chemically stiffened, twisted, curled cellulosic fibers and from 0% to about 50%, or more preferably from 0% to about 25% by weight of a binding agent for such fibers.

2. Fluid Storage Component

In addition to the upper and lower acquisition components 28 and 34, the absorbent structure 26 further comprises a storage component 36 which is maintained in fluid communication with the acquisition components 28 and 34 so that body exudates present in the acquisition components 28 and 34 can be distributed for optimal absorption by the storage component 36. The principal function of the storage component 36 is to absorb, redistribute and store discharged body exudates from the acquisition components 28 and 34, and to retain such exudates under the pressures and stresses encountered as a result of the wearer's movement. Some of the fluid handling and absorbency characteristics which have been identified as being important to the realization of suitable fluid storage component 36 are, the ability of the storage component 36 to drain exudates from the other components of the absorbent article 20 and vertical wicking ability.

Ideally, the storage component 36 will quickly pull or drain exudates from other components in the absorbent article 20 (e.g., the topsheet 22 or the components 28, 34 or 36) which is known in the industry as partitioning ("dewatering"). The material of the storage component 36 should exhibit especially desirable fluid partitioning characteristics relative to the upper and lower acquisition components 28 and 34. In particular, the extent to which the storage component 36 partitions exudates from the lower acquisition component 34 provides an overall softer absorbent structure 20.

Yet another fluid handling attribute useful in the storage component 36 relates to the ability to relatively quickly move or transport acceptable amounts of body exudates through their foam structures. Vertical wicking (i.e., fluid wicking in a direction opposite from gravitational force) is one measure of the especially desirable performance attribute of fluid transport for the storage component absorbent materials herein. This is especially true with an absorbent article 20 having a lower acquisition component 34 since absorbed exudates must often be moved from a relatively lower position in the acquisition component 34 to a relatively higher position within the storage component 36.

It is possible to select certain combinations of parameters which will provide materials that exhibit especially desirable mechanical properties for storage component 36. The specific, somewhat interrelated mechanical properties which have been identified as contributing to their suitability for use in absorbent articles 20 for incontinence management are resistance to compression deflection, flexibility, recovery from compression deflection (e.g., resilience), foam integrity, and softness to the touch. 20 The storage component 36 of the diaper, illustrated in FIG. 2, has a front region 36a worn around a wearer's front, a back region 36c worn around a wearer's back side, and a crotch region 36b lying between the front and back regions 36a and 36b respectively, that is intended to be worn in the area of a wearer's crotch.

The storage component 36 can be configured to have a smaller surface area than both the upper and lower acquisition component 28 and 34 and still effectively and efficiently absorb, redistribute and store fluids from both the upper and lower acquisition components 28 and 34. The surface area of the storage component 36 will generally range from about 30% to about 100% of the surface area of the lower acquisition component 34 and will range from about 30% to about 100% of the surface area of the upper acquisition component 28.

The storage component 36 will have a length smaller than the length of both the upper and lower acquisition components 28 and 34. As stated previously, the width of the storage component 36 is the same as the width of both the upper and lower acquisition components 28 and 34 at the front and back portions 34a and 34c respectively, however, it is important to note that the width of the storage component 36 can be narrower than the width of both the upper and lower acquisition components 28 and 34 at the crotch area 36b. The storage component 36 can be of any desired shape consistent with comfortable fit and the sizing limitations discussed above. A preferred embodiment provides a storage component 36 having a width of about 2.5" (6.35 cm) at the crotch portion 36b, especially when storage component 36 comprises a flexible, hydrophilic polymeric structure of interconnected open spaces, described in greater detail below.

The individual components of the absorbent article 20, namely the topsheet 22, backsheet 24, the upper and lower acquisition components 28 and 34, and the fluid storage component 36, and its various layer(s) are assembled using techniques known in the art.

i. Polymeric Foam

Suitable materials usable in or as the storage component 36 include a polymeric structures, and preferably, a hydrophilic, flexible, polymeric structure of interconnected open spaces. The structure can be a foam material, such as the type disclosed in U.S. Pat. Nos. 5,147,345, to Young, et al.; 5,260,345, to DesMarais, et al.; U.S. Pat. No. 5,387,207, issued Feb. 7, 1995 to Dyer, et al.; and commonly assigned, U.S. patent application, Ser. No. 08/370,922, filed Jan. 10, 1995, in the names of Thomas A. DesMarais, et al., the disclosures of which are incorporated herein by reference.

In a preferred embodiment, the storage component 36 comprises a plurality of multiple layers of a foam material that provides both improved fluid-holding characteristics and improved softness, and its overall thickness is dictated by the desired absorbent capacity of the foam structure. For example, the storage component 36 comprising a polymeric foam material operates and effectively stores discharged body fluid in the form of an infant disposable diaper when it has an overall thickness of from about 0.15" to about 1.50" (0.38 to 3.81 cm), and more preferably from about 0.25" to about 0.75" (0.64 to 1.91 cm). It has been found that the fluid storage structures can be configured with one layer or a plurality of individual layers, such as two to five, of a polymeric foam material, and preferably three layers of a polymeric foam material (see FIGS. 3–5), with each layer preferably having at thickness of about 0.145" (3.7 mm) and an overall thickness of about 0.44" (1.14 cm).

Polymeric foam materials which are useful in the storage component 36 are those which possess performance (e.g., fluid handling) properties which render such foams especially suitable and useful as absorbents for the exudates being absorbed. These fluid handling characteristics are, in turn, related to and determined by the structural and mechanical characteristics of the absorbent foam materials. Foams having a specific set of structural and mechanical properties can, in fact, be used as absorbent materials in the storage component 36 because they will provide the requisite fluid handling characteristics, as discussed above.

ii. Superabsorbent

Another suitable material used in or as the storage component 36 is a combination of a superabsorbent material, such as a polymeric gelling material (also known as a hydrogel-forming material) incorporated into a fibrous web or tissue, such as the type disclosed in U.S. Pat. No. 5,217,445, the disclosure of which is hereby incorporated herein by reference.

The storage component 36 can comprise a superabsorbent material such as, but not necessarily limited to, discrete particles of absorbent gelling material and superabsorbent fibrous material such as acrylate grafted fibers and superabsorbent modified fibers. The superabsorbent material can be in any form which can be incorporated into a flexible web or sheet to form the storage component 36. The superabsorbent material, upon contact with exudates, absorb the exudates. In this manner, exudates discharged into the acquisition components 28 and 34 are transported to the storage component 36 can be acquired and held by the superabsorbent material, thereby providing the article 20 with enhanced absorbent capacity and/or improved fluid retention performance.

The superabsorbent material of the present invention utilized in the form of discrete particles of absorbent gelling material which will be distributed within a web of fibrous material, such as tissues synthetic fibers, natural fibers, or a combination of both, as carrier means. A suitable fibrous carrier means are cellulose fibers, in the form of fluff, such as is conventionally utilized in an absorbent structure 26 of the present invention. Modified cellulose fibers, such as the stiffened cellulose fibers described above, can also be used. Synthetic fibers can also be used and include those made of cellulose acetate, polyvinyl fluoride, polyvinylidene chloride, acrylics (e.g., orlon), polyvinyl acetate, non-soluble polyvinyl alcohol, polyethylene, polypropylene, polyamides (e.g., nylon), polyesters, bicomponent fibers, tricomponent fibers, mixtures thereof and the like. The fiber surfaces are hydrophilic or are treated to be hydrophilic.

Within the storage component 36 of the present invention, the superabsorbent material can be uniformly distributed, or alternatively, there may be regions which have higher concentrations of superabsorbent material.

In accordance with the above discussion, disposable diapers can be configured in the following non-limiting manner. As mentioned earlier, the upper acquisition components 28 can, for example, comprise: a polymeric foam material, airfelt, or a chemically stiffened cellulose fiber material. Furthermore, the storage component 36 and lower acquisition component 34 can comprise a hydrophilic flexible structure of interconnected open spaces, such as a polymeric foam material.

It is presently preferred that both the lower acquisition component 34 and the storage component 36 comprise a polymeric foam material, or that the lower acquisition component 34 comprise a polymeric foam and the storage component 36 comprise a polymeric gelling material incorporated into a fibrous web or tissue.

Having shown and described the preferred embodiments of the present invention, further adaptions of the high efficiency absorbent articles for incontinence management described herein can be accomplished by appropriate modifications by one of ordinary skill in the art without departing from the scope of the present invention. Several such potential modifications have been mentioned, and others will be apparent to those skilled in the art. For example, other materials having the above-discussed characteristics can be substituted for the upper and lower acquisition components and the storage component. In addition, the absorbent product can take the shape of article other than disposable diapers, such as bandage dressing, sanitary napkins, or other articles that absorb, redistribute and retain fluid, even when subjected to compression forces. Accordingly, the scope of the present invention should be considered in terms of the following claims and is understood not to be limited in detail, structure and operation shown and described in its specification and drawings.

We claim:

1. An absorbent article for the management of body exudates, said article comprising:
   a) a back sheet;
   b) a top sheet; and
   c) an absorbent structure interposed between said back sheet and said top sheet, and comprising:
      i) an upper acquisition component interposed in close proximity to said top sheet;
      ii) a lower acquisition component adjacent said back sheet and having original dimensions, said lower acquisition component comprising a material capable of providing desorption pressures and a recovery from wet compression of about 60% of said original dimensions; and
      iii) a storage component interposed between said upper and said lower acquisition components and being in fluid communication with said lower acquisition component, and capable of providing an absorption pressure, said capillary desorption pressures of said lower acquisition component being less than said absorption pressures of said storage component.

2. The absorbent article of claim 1, wherein each of said lower acquisition and storage components comprises a flexible, hydrophilic polymeric structure of interconnected open spaces.

3. The absorbent article of claim 1, wherein said storage component comprises a polymeric gelling material.

4. The absorbent article of claim 1, wherein said upper acquisition component comprises a flexible, hydrophilic polymeric structure of interconnected open spaces.

5. An absorbent article for the management of fluids, said absorbent article comprising:
   a) a back sheet;
   b) an absorbent structure comprising;
      i) a storage component capable of providing an absorption pressure, and
      ii) a lower acquisition component interposed between said back sheet and said storage component and adjacent said back sheet, said lower acquisition component capable of providing capillary desorption pressures, said absorbent pressure of said storage component being greater than said capillary desorption pressures of said lower acquisition component whereby fluid in said lower acquisition component is capable of being partitioned from said lower acquisition component to said storage component.

6. The absorbent article of claim 5, wherein said lower acquisition component comprises a hydrophilic, flexible structure of interconnected open spaces.

7. The absorbent article of claim 5, wherein said storage component comprises a hydrophilic, flexible structure of interconnected open spaces.

8. The absorbent article of claim 5, wherein said storage component comprises a polymeric gelling material.

9. The absorbent article of claim 5, wherein said absorbent structure comprises an upper acquisition component, and said storage component is interposed between said upper and lower acquisition components.

10. The absorbent article of claim 9, wherein said upper acquisition component comprises first and second upper acquisition components, each of said first and second upper acquisition components having an average pore size diameter, said second upper acquisition component interposed between said first upper acquisition component and said storage component, and said average pore size diameter of said second upper acquisition component being less than said average pore size diameter of said first upper acquisition component.

11. The absorbent article of claim 9, wherein said upper acquisition component comprises a hydrophilic, flexible structure of interconnected open spaces.

12. The absorbent article of claim 9, wherein said upper acquisition component comprises a non-woven fibrous structure.

13. The absorbent article of claim 9, wherein said upper acquisition component comprises hydrophilic chemically stiffened cellulosic fibers.

14. The absorbent article of claim 5, wherein each of said storage component and said lower acquisition component comprises a crotch portion, said crotch portion of said lower acquisition component having a width at least about 5% greater than said crotch portion of said storage component.

15. The absorbent article of claim 5, wherein each of said lower acquisition component and said storage component comprises a surface area, the surface area of said lower acquisition component being greater than the surface area of said storage component.

16. The absorbent article of claim 5, wherein said lower acquisition component has original dimensions, and comprising a material being capable of a recovery from wet compression of at least about 60% of said original dimensions.

17. The absorbent article of claim 5, wherein said lower acquisition component comprises a material being capable of a resistance to compression deflection.

18. The absorbent article of claim 17, wherein said lower acquisition component comprises a material being capable of a resistance to compression deflection such that a confining pressure of about 5.1 kPa produces a strain between about 5%–85% compression of said lower acquisition component.

19. The absorbent article of claim 5, comprising a top sheet and wherein said storage component is interposed between said top sheet and said lower acquisition component.

20. The absorbent article of claim 5, wherein said lower acquisition comprises a material having a capacity from about 12 grams to about 125 grams of synthetic urine per gram of said lower acquisition component.

21. The absorbent article of claim 5, wherein said lower acquisition component comprises an average pore size from about 20 to about 200 $\mu$m.

* * * * *

UNITED STATES PATENT AND TRADEMARK OFFICE
CERTIFICATE OF CORRECTION

PATENT NO. : 5,817,081
DATED : October 6, 1998
INVENTOR(S) : LaVon et al.

It is certified that error appears in the above-identified patent and that said Letters Patent is hereby corrected as shown below:

Column 4,
Line 2, after "elastic" delete ":" (the colon).
Line 18, delete "turns" and insert therefore -- turn --.

Column 5,
Line 16, after "thereof" insert therefore -- . —(a period).
Line 23, after "polyester" delete "." (the period).

Column 6,
Line 27, after "components" delete "29" and insert therefore -- 28 --.

Column 12,
Line 57, delete "all" and insert therefore -- an --.
Line 62, delete ":" (the colon) between "0" and "3".

Column 14,
Line 63, after "touch." delete "20" and insert paragraph break before "The".

Signed and Sealed this

Ninth Day of July, 2002

Attest:

Attesting Officer

JAMES E. ROGAN
Director of the United States Patent and Trademark Office